United States Patent [19]

Ota et al.

[11] 4,334,610

[45] Jun. 15, 1982

[54] METHOD OF STORING A SOLID CHLORINATING AGENT AND AN ARTICLE FOR STORING SAME

[75] Inventors: Masanori Ota; Toshiki Mori; Tokuyuki Taniguchi, all of Funabashi, Japan

[73] Assignee: Nissan Chemical Industries, Ltd., Japan

[21] Appl. No.: 112,915

[22] Filed: Jan. 17, 1980

[30] Foreign Application Priority Data

Jan. 23, 1979 [JP] Japan .................................. 54-6455
Nov. 16, 1979 [JP] Japan .............................. 54-148366

[51] Int. Cl.³ ...................... B65D 81/24; C01B 11/02; C11D 3/395; C11D 7/54
[52] U.S. Cl. ................................. 206/205; 53/111 R; 53/111 RC; 206/213.1; 252/95; 422/9; 422/10
[58] Field of Search ................. 252/187 C, 187 H, 95; 422/9, 10; 53/111 R, 111 RC; 206/205, 213.1; 8/108 A

[56] References Cited

U.S. PATENT DOCUMENTS

| 1,657,272 | 1/1928 | Neusbaum | 206/205 |
|---|---|---|---|
| 2,719,660 | 10/1955 | Ellis | 206/213.1 |
| 2,988,471 | 6/1961 | Fuchs et al. | 252/187 C |
| 3,061,549 | 10/1962 | Dickey | 252/99 |
| 3,108,079 | 10/1963 | Wixon | 252/99 |
| 3,183,057 | 5/1965 | Marks et al. | 206/213.1 |
| 3,528,921 | 9/1970 | Gray | 252/99 |
| 3,577,347 | 5/1971 | Mosick | 252/99 |

FOREIGN PATENT DOCUMENTS

| 2340910 | 2/1974 | Fed. Rep. of Germany . |
|---|---|---|
| 41-8069 | 4/1966 | Japan . |
| 43-18778 | 8/1968 | Japan . |
| 45-10065 | 4/1970 | Japan . |
| 45-21379 | 7/1970 | Japan . |
| 816882 | 7/1959 | United Kingdom . |

*Primary Examiner*—Irwin Gluck
*Attorney, Agent, or Firm*—Stevens, Davis, Miller & Mosher

[57] ABSTRACT

A method of storing a solid chlorinating agent with improved storage performance involving placing the solid chlorinating agent and a storage stabilizer such as calcium oxide, trisodium phosphate, magnesium oxide, ferrous oxide, melamine, ammeline or ammelide in a closed container in a manner that the stabilizer contacts the noxious gases in the same container but not with the solid chlorinating agent in the same container. An article for storing the same is composed of a closed container in which the solid chlorinating agent is placed together with the storage stabilizer in such a manner that the gases are brought into contact with the storage stabilizer.

28 Claims, 1 Drawing Figure

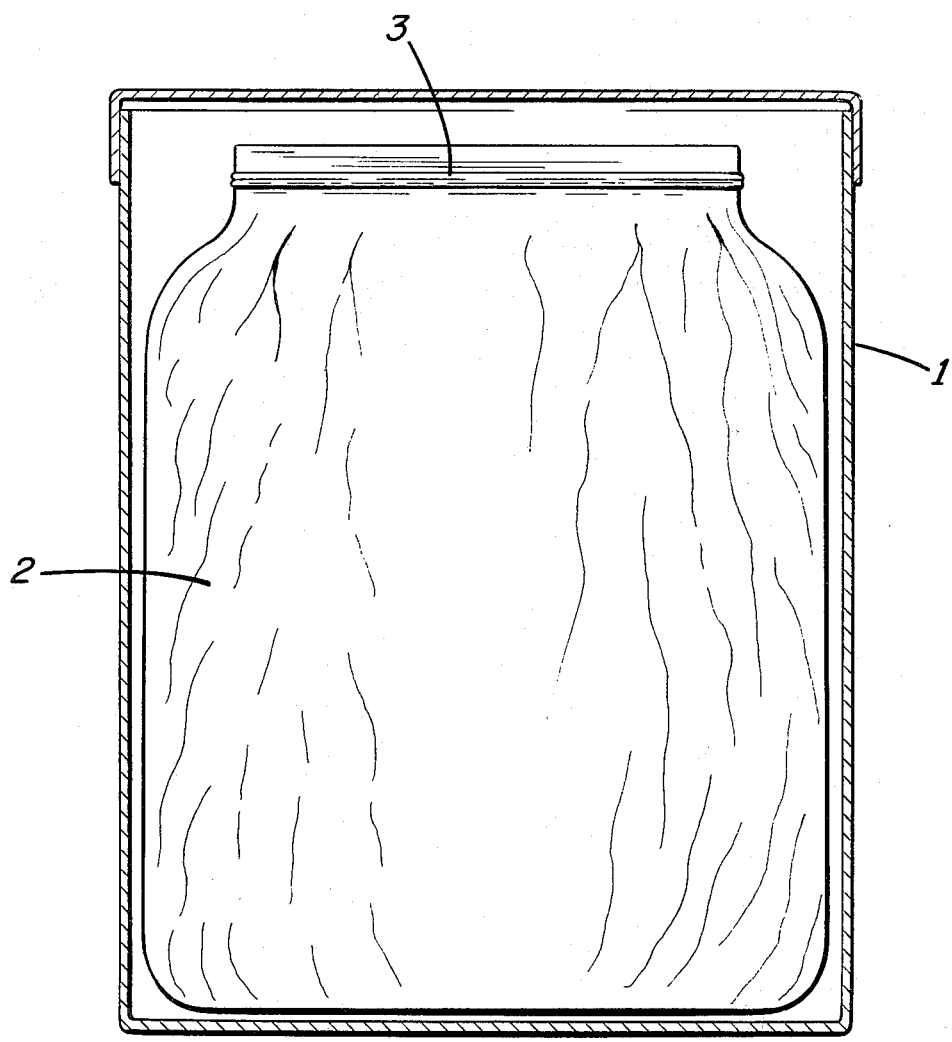

METHOD OF STORING A SOLID CHLORINATING AGENT AND AN ARTICLE FOR STORING SAME

BACKGROUND OF THE INVENTION

1. Field of the Invention

The present invention relates to a process of storing a solid chlorinating agent which tends to generate gases such as chlorine gas and nitrogen chloride gas upon decomposition during storage.

2. Brief Description of the Prior Art

Solid chlorinating agents have been widely employed commercially in various fields as disinfectants, germicides, bleaching agents and the like. Such solid chlorinating agents include trichlorinated and dichlorinated isocyanuric acid, anhydrides and hydrates of sodium and potassium dichlorinated isocyanurate and a mixture thereof and a composition thereof with auxiliary agents. These agents have been used in various forms such as powders, granules, grains and tablets.

These solid chlorinating agents are usually stored and transported in closed packing containers such as paper bags, plastic containers and metallic cans. Since the solid chlorinating agents will often be stored for a period of time of as long as one or two years after manufacture before they are actually used on site, noxious gases will be generated during storage upon decomposition of the solid chlorinating agents and those gases may exert undesirable influences, causing in rare cases dangerous incidents. For example, such noxious gases may causes label information on a container to become unclear or fade away completely. The gas generation also may cause the corrosion of packing materials or the breakdown of containers themselves from an increase in internal pressure therein. The gases may give off offensive odors to users or an unpleasant feeling upon opening of a packing container anywhere or during use on the site. Further, the gases generated by decomposition of the solid chlorinating agents are noxious and hazardous to the human body.

Accordingly, many attempts have been made so far to overcome those difficulties and disadvantages involved in the generation of the noxious gases. One attempt is to decrease the water content in the product, thereby preventing the generation of the gases upon decomposition during storage. However, it is almost practically impossible to industrially manufacture products virtually free of water. It also has been attempted to store the product under an atmosphere where outside moisture is completely blocked. For this purpose, where containers composed of a metallic material capable of blocking the outside moisture are used, the metallic material may be subject to corrosion or transformation and even broken during long periods of storage by the accumulation of the decomposed gases. A further attempt also has been made to prepare the product in granular or tablet form thereby decreasing the specific surface area of the product and, as a consequence, preventing the generation of the gases. However, these methods are not satisfactory for storing over a long period of time. It also has been proposed that the solid chlorinating agents be coated with a film such as paraffin wax or polyvinyl alcohol. The effect of this coating is not extensive enough and is not desired for use in disinfecting pool water because the coating may provide the water with oily substances. The addition of desiccants such as potash alum to the solid chlorinating agents to form a composition also has been proposed; however, the effect is not satisfactory.

It further has been proposed that a stabilizer such as limonene be added to the solid chlorinating agent in order to prevent the decomposition of the agent. The effect of the addition of this stabilizer is not enough, and sometimes may even accelerate the generation of gases or cause a yellow coloring on the agent.

SUMMARY OF THE INVENTION

Accordingly, it is an object of the present invention to provide a method of conveniently storing a solid chlorinating agent including trichlorinated isocyanuric acid, dichlorinated isocyanuric acid, sodium or potassium dichlorinated isocyanurate, bleaching powder containing calcium hypochlorite or sodium chlorite or a mixture threof in a closed container for a long period of time, to prevent the generation of noxious gases, by adsorbing effectively the gases generated by natural decomposition, and prevent the damage or breakdown of the container surface or materials or the diffusion of the noxious gases or offensive odors upon opening of the container.

Another object of the present invention is to provide a method of storing for a prolonged period of time the solid chlorinating agent in a closed container without a decrease in efficiencies and transformation or coloring of the agent and further without existence of undesirable foreign materials when used on the site.

A further object of the present invention is to provide a packing container to store the solid chlorinating agent for a long period of time, without the accelerated generation of the noxious gases or offensive odors upon the opening of the container and with improved storage characteristics.

BRIEF DESCRIPTION OF THE DRAWING

The drawing shows one embodiment of a storage article of the present invention.

DETAILED DESCRIPTION OF THE INVENTION

The storing method in accordance with the present invention is accomplished by placing a solid chlorinating agent together with a specific storage stabilizer in a closed container in such a manner that the storage stabilizer does not contact the solid chlorinating agent but is accessible to gases formed from the solid chlorinating agent in the closed container.

The solid chlorinating agent to be used for the method of the present invention may contain trichlorinated or dichlorinated isocyanuric acid, anhydrides or monohydrates of sodium or potassium dichlorianted isocyanurate, dihydrate of sodium dichlorinated isocyanurate, bleaching powder of calcium hypochlorite, sodium chlorite or a mixture thereof. The agent may be in any form and may be in powdery, granular or tabletted form. The chlorinating agent as an industrial product, which is virtually free of water, is hardly obtainable and usually contains water in a very small amount. Such solid chlorinating agent has a property to generate decomposed gases such as chlorine gas, nitrogen chloride gas, and the like even when stored in a closed container, and it is likely in nature to generate such gases when stored in a container such as plastic bags or paper drum having a slight air permeability. The solid chlorinating agent may also usually contain various auxiliary materials which may be added thereto depending on the purposes of use. The method of the present invention may also be applicable to such solid chlorinating agent as N-chloroimides and N-chloroamides, which may generate said gases upon decomposition.

The storage stabilizer to be used in the present invention includes trisodium phosphate, calcium oxide, magnesium oxide, ferrous oxide, melamine, ammeline or ammelide or a mixture thereof. The storage stabilizers may be used alone or in combination with each other and usually in granular, powdery, grainy or tabletted form or as a composition where one or more of the storage stabilizers may be finely dispersed in a plastic material including, for example, polyolefinic resins such as polyethylene, copolymers of ethylene and propylene, butene, vinyl acetate, or the like, polypropylene or a mixture thereof, polyvinyl chloride resins such as polyvinyl chloride, copolymers of vinyl chloride and ethylene, propylene, vinyl acetate or other copolymeric monomer and polymers of vinylidene chloride and copolymers thereof with other copolymerizable monomers. The composition to be used in the present invention may be preferably prepared by mixing the storage stabilizer and the plastic material under the molten state of the plastic material and then permitting the mixture to solidify by cooling it to room temperature. The composition may usually be molded to a desired shape such as granules or pellets, filaments, sheets, films or plates. The storage stabilizer may be used in an amount of from about 0.1 to about 10 percent by weight and preferably from about 0.3 to about 5 percent by weight with respect to the weight of the solid chlorinating agent to be stored in a closed container. The amount of the storage stabilizer to be placed with the solid chlorinating agent in a closed container may be varied depending upon the material of a container in which the agent is stored, the temperature of storage, duration of storage and the like. For example, an amount as much as 1 percent by weight based on the solid chlorinating agent is enough where the agent is stored in a closed metal container. In this case, no odors associated with the decomposition of the solid chlorinating agent was perceived even after storage for 30 days at room temperature.

The storage stabilizer to be used in the present invention may be arranged under closed circumstance in such a manner that the stabilizer is placed in contact with the ambient gas. The terms "closed circumstance" referred to throughout the specification and claims are intended to mean a closure around the chlorinating agent intercepting the outside atmosphere from the chlorinating agent. Such a closed circumstance usually contains air, gases generated from the solid chlorinating agent upon decomposition and the atmospheric air permeated from the outside atmosphere when stored in a container composed of materials capable of permeating air to an extremely slight extent. The closed container to be used for storage in the present invention may be of any shape which may be appropriate for packing, storage, and transportation and may be in the form of paper bags or boxes, plastic film bags or molded containers, metal cans, fiber drums, and the like. Containers such as apparatus, vessels, mixers or the like, for example for the manufacturing of the solid chlorinating agent, having a vent, may also be employed for temporary storage when the storage is conducted without forced ventilation and where a closed circumstance may be formed within the inside of said container where the solid chlorinating agent is stored.

In accordance with the present invention, the solid chlorinating agent is placed together with the storage stabilizer in a closed container in such a manner that the gases generated by the decomposition of the solid chlorinating agent are brought into contact the storage stabilizer perse, but that the storage stabilizer does not contact with the solid chlorinating agent. The mode of arrangement for placing the agent to be stored and the stabilizer in a closed container is not limited to any particular one. Where the container to be used for storage is composed of a material tending to be damaged or othewise adversely affected by the presence of the agent to be stored, the gases generated therefrom and/or the stabilizer, the arrangement of placing should be made in a manner such that they are not brought into contact with the inner surface of the container.

When the stabilizer is employed in the form of, for example, powders, granules, grains and tablets, the stabilizer should be placed in such a manner that it is not brought into direct contact with the solid chlorinating agent. In this case, the stabilizer may be packed in a container, for example, a bag, composed of a material such as paper or plastic sheeting having pores small enough to permit the gases to pass therethrough, but preventing penetration and passage of both the chlorinating agent and the stabilizer, and tending to be indestructible with respect to the agent to be stored, the gases generated therefrom and/or the stabilizer. The mode of placing the stabilizer is, for example, merely placing the packages of the stabilizer anywhere around the agent to be stored within spaces defined in the container.

The storage stabilizer compositions as prepared hereinabove from the stabilizer and the polymer resins may be preferably employed in place of the stabilizer packages as hereinabove. This is one of the preferred embodiments of the present invention, whereby the purposes of the present invention can be conveniently achieved. The composition to be used in the present invention may contain from about 10 to about 60 percent by weight of the stabilizer. The composition may also contain additives such as auxiliary substances for processing, fillers and other stabilizer as long as they do not adversely affect the effect of the stabilizer in the composition. The composition may be preferably employed in a form of granules, pellets, filaments, films, sheets or plates which may be prepared in such as manner as having pores small enough to permit the penetration of the gases to be adsorbed, but disallow the leakage of the stored agent. They may be easily prepared in conventional manner, for example, by mixing with mixing rolls or screw extruders and molded into desired shapes such as granules, pellets, filaments, films sheets, plates, bags and other containers. The composition of the stabilizer in the granule, pellet, filament, film, sheet or plate forms may be used, as a preferred embodiment of the present invention, merely by placing it anywhere around the agent in a space defined among the solid chlorinating agents in the container. The bags or containers made of the composition may also be used, as another preferred embodiment of the invention, into which the solid chlorinating agent may be placed for storage. These bags or containers, which are sealed in conventional manner, may be used alone for storage without an outer case to contain them for a relatively short period of time and may be transported as they are.

The bags or containers made of the compositon contained with the agent also may be more preferably placed in another outer container or case more rigid than the former for enduring a longer term of storage.

This is shown in the drawing, wherein 1 represents an outer, rigid container made of material such as cardboard. Bag 2 incorporates the stabilizer and a plastic such as polyethylene. The stabilizer is preferably mixed into the polyethylene when the polyethylene is molten. The chlorinating agent is packed in bag 2 which is sealed at its upper end by conventional means as shwn by 3.

In the preferred embodiments of the present invention mentioned immediately hereinabove, surprisingly, there occurs neither the generation of gases by decomposition nor the transformmation of the solid chlorinating agent in spite of being in contact with the solid chlorinating agent in a form of powder, granule, grain or tablet with the surface of the storage stabilizer composition, i.e. granule, pellet, filament, film, sheet or plate. These effects described hereinabove may be considered to be based on substantially negligible amounts of the direct contacting of the solid chlorinating agent with the stabilizer, if any.

When the stabilizer itself is used directly in the form of powders, granules or tablets and in direct contact with the solid chlorinating agent as in the case of being mixed with the agent or being employed as a coating on the surface of the agent, the decomposition of the agent is accelerated, thereby resulting in the increase of the noxious gases in the closed container. This is obviously contrary to the purposes of the present invention. Further, the storage stabilizer should be arranged to be brought into contact with the gases generated from the solid chlorinating agent. If the stabilizer were not contacted with the gases, it is without doubt clear that no effect from the use of the stabilizer is accomplished.

When the storage stabilizer is placed in a closed container in accordance with the method of the present invention, it has now been found that the decomposition of the solid chlorinating agent is not accelerated and the storage stabilizer can strongly adsorb and fix thereon the noxious gases generated from the agent during storage. Accordingly, the storage stabilizer of the present invention hardly causes transformation or coloring of the solid chlorinating agent stored. The effect of the employment of such storage stabilizer is remarkable and can not be achieved by the use of conventional agents such as activated carbon, activated clay, sodium chloride, sodium sulfate, calcium fluoride, aluminum hydroxide, ferric oxide, and acidic sodium phosphate. Further, in accordance with the present invention, the solid chlorinating agent may be stored for a long period of time with safety and stability. And the present invention does not generate gases and produce hazardous and undesirable odors upon opening of the container where the agent is stored.

The following examples illustrate the present invention more in detail, but should not be construed as limiting the present invention thereto.

REFERENCE EXAMPLE 1

Twenty grams of granular trichloroisocyanuric acid having a particle diameter of 0.25-1.4 mm, a water contant of 0.13 percent and an effective chlorine content of 90.7 percent were charged into a three-necked glass container with one of the necks (first neck) closed with a rubber lid and with the other two (second and third necks) closed with a plug equipped with a valve. The container was placed for given days in a room where the temperature was maintained at 35° C. The second neck was then connected to a tube through which dry nitrogen gas was passed into the container, and the third was connected to a tube through which the inner gas was led to 80 ml of 1% ortho-tolidine hydrochloride aqueous solution. After the completion of storage, the dry nitrogen gas was then introduced from the second neck into the container and the inside air was introduced from the third neck into the ortho-tolidine aqueous solution in which the decomposed gas present therein was absorbed.

The solution was measured by means of a spectrophotometer for the absorbance of yellow light at a wavelength of 400 m$\mu$. The measurement was made after storage of 3 days, 10 days, and 30 days. Table 1 below indicates the measured results where the reading of the spectrophotometer measured with respect to the 30 days storage was referred to at "100".

EXAMPLES 1-4

The procedure of Reference Example 1 was repeated with the exception that a bag of porous polyvinyl chloride film 0.12 mm thick containing a stabilizer as mentioned in Table 1 was hung below the glass lid closing the first neck of a container in a manner that the bag is not in contact with trichloroisocyanuric acid to be tested. The results will be shown in Table 1.

COMPARATIVE EXAMPLES 1-7

The procedure of Example 1 was repeated except that 1 gram of a stabilizer as mentioned in Table 1 was employed in place of the stabilizer of Examples 1 to 4. Table 1 shows the results which indicate that the stabilizers used in Comparative Examples were considered to be not appropriate.

TABLE 1

| Examples | Stabilizers | Amounts of Gases Generated | | |
|---|---|---|---|---|
| | | 3 Days | 10 Days | 30 Days |
| Reference Example 1 | None | 32 | 62 | 100 |
| Example 1 | Calcium oxide | 0 | 0 | 1 |
| Example 2 | Trisodium phosphate | 3 | 5 | 10 |
| Example 3 | Ferrous oxide | 5 | 10 | 10 |
| Example 4 | Magnesium oxide | below 1 | below 1 | 2 |
| Comparative Example 1 | Activated carbon | 5 | 20 | 105 |
| Comparative Example 2 | Activated clay | 15 | 90 | 95 |
| Comparative Example 3 | Zeolite | 10 | 25 | 70 |
| Comparative Example 4 | Sodium chloride | 35 | 71 | 105 |
| Comparative Example 5 | Sodium sulfate | 35 | 70 | 107 |
| Comparative Example 6 | Calcium iodide | 6 | 30 | 80 |
| Comparative Example 7 | Calcium fluoride | 30 | 60 | 105 |

REFERENCE EXAMPLE 2

One kilogram of the trichloroisocyanuric acid as employed in Reference Example 1 was charged into a 200×300 mm high density polyethylene bag having a film thickness of 0.15 mm with one open end of the bag connected to a tube charging dry nitrogen and to a tube leading to the tolidine solution as used above and the bag was heat sealed. The bag was stored for 15 days in a room at a relative humidity of 60 percent and a temperature of 35° C. The gases generated by decomposition were measured in the same manner as in Reference Example 1 and the amount of the gases absorbed in the orthotolidine solution was referred as to "100".

EXAMPLES 5-9

The procedure of Reference Example 2 was repeated with the exception that 10 grams of a stablizer as listed in Table 2 were placed in a 40×50 mm porous high density polyethylene bag having a film thickness of 0.15 mm. The results will be shown in Table 2. The odors were determined olfactorily by smelling with one end of the bag open. The results will also be shown in Table 2.

COMPARATIVE EXAMPLES 8-11

The procedure of Example 5 was repeated except that a stabilizer as mentioned in Table 2 was employed in place of the stabilizer of Examples 5 to 9. The results will be shown in Table 2 and indicate that the stabilizers used for comparative purposes regarded as not good.

TABLE 2

| Examples | Stabilizer | Amount of Gases Generated After 15 Day Storage | Odors After 15 Day Storage |
|---|---|---|---|
| Reference Example 2 | None | 100 | Extremely Strong |
| Example 5 | Calcium oxide (powders) | 0 | Not at all |
| Example 6 | Calcium oxide (bulk) | 1 | Not at all |
| Example 7 | Magnesium oxide | 2 | Not at all |
| Example 8 | Trisodium phosphate | 7 | Not at all |
| Example 9 | Ferrous oxide | 10 | Hardly |
| Comparative Example 8 | Aluminum oxide | 50 | Strong |
| Comparative Example 9 | Aluminum hydroxide | 90 | Extremely Strong |
| Comparative Example 10 | Ferric oxide | 100 | Strong |
| Comparative Example 11 | Tri-iron tetroxide | 100 | Extremely Strong |

EXAMPLES 10-12

The procedure of Example 1 was repeated with the exception that 50 grams of sodium dichloroisocyanurate powders having a particle diameter of smaller than 0.074 mm, a water content of 1.5 percent, and an effective chlorine content of 60.7 percent and a stabilizer as listed in Table 3 were employed in place of trichloroisocyanuric acid and calcium oxide. The results will be shown in Table 3.

COMPARATIVE EXAMPLES 12-13

The procedure of Example 10 was repeated with the exception that a stabilizer as listed in Table 1 was employed in place of the stabilizer of Example 10. The results will be shown in Table 3 and indicate that the stabilizers used for comparative purposes were considered to be not good.

TABLE 3

| Examples | Stabilizer | Amounts of Gases Generated | | |
|---|---|---|---|---|
| | | 3 Days | 10 Days | 30 Days |
| Reference Example 3 | None | 17 | 33 | 100 |
| Example 10 | Calcium oxide | 0 | 0 | 1 |
| Example 11 | Ferrous oxide | 4 | 5 | 10 |
| Example 12 | Trisodium phosphate | 1 | 2 | 7 |
| Comparative Example 12 | Sodium monohydrogen phosphate | 7 | 16 | 100 |
| Comparative Example 13 | Sodium dihydrogen phosphate | 15 | 35 | 100 |

REFERENCE EXAMPLES 4-5

Two hundred grams of trichloroisocyanurate were charged into a 160×220 mm of polyvinyl chloride film having a thickness of 0.12 mm (Reference Example 4) and of high density polyethylene having a film thickness of 0.12 mm (Reference Example 5). The bag after sealed was then stored for 30 days. The amounts of the gases decomposed were determined in the same manner as described in Reference Example 2. The results will be indicated in Table 5.

EXAMPLES 13-15

The procedure of Reference Example 4 was repeated with the exception of a plastic sheet as listed in Table 4. The results are shown in Table 5.

TABLE 4

| Examples | Components (by weight) | | | |
|---|---|---|---|---|
| | Resin | Resin | Additive | Calcium oxide |
| 13 | High density polyethylene | 48 | 2 (calcium stearate) | 50 |
| 14 | High density polyethylene | 68 | 2 (calcium stearate) | 30 |
| 15 | Polyvinyl chloride | 40 | 30 (plasticizer) | 30 |

TABLE 5

| Examples | Amounts of Gases Generated |
|---|---|
| Reference Example 4 | 100 |
| Reference Example 5 | 100 |
| Example 13 | 1 |
| Example 14 | 3 |
| Example 15 | 1 |

EXAMPLE 16

Fifty grams of trichloroisocyanuric acid having a particle diameter of 0.25-1.4 mm, a water content of 0.15 percent and an effective chlorine content of 90.3 percent were charged into a 200 ml three-necked glass container. Two grams of melamine powders were introduced into a porous polyvinyl chloride bag having a film thickness of 0.12 mm. The first neck of the container was closed with a rubber lid with the bag containing the melamine powders hung below. The second neck thereof was equipped with a valved glass plug which was in turn connected to a tube through which dry nitrogen gas was passed into the container. The opening of the third neck thereof was closed with a valved glass plug connected through a tube to 100 ml of 1% ortho-tolidine hydrochloride aqueous solution.

The container containing the solid chlorinating agent was stored at 35° C. for 5 days with all three valves closed. The nitrogen gas was then introduced through the second neck into the container, and the air in the container was passed into the ortho-tolidine solution, thereby absorbing the decomposed gases therein and turning the color of the solution yellow. The solution was measured for the absorbance of yellow light at a wavelength of 440 mµ by means of a spectrophotometer. The results will be shown in Table 6 in which the amount of gases generated was calculated as an amount of total chlorine gas.

EXAMPLES 17–18

The procedure of Example 16 was repeated with the exception that high test calcium hypochlorite, a reagent of first grade, having a particle diameter of 0.1–0.35 mm, a water content of 0.24 percent and an effective chlorine content of 68.04 percent (Example 17) and sodium chlorite having a particle diameter of 0.3–1.0 mm, a water content of 0.11 percent and an effective chlorine content of 69.7 percent (Example 18), respectively, were employed in place of trichloroisocyanuric acid. The results will be indicated in Table 6.

COMPARATIVE EXAMPLES 14–16

The procedures of Examples 16 to 18, respectively, were repeated with the exception that the bag containing melamine powders was not used. The results will be shown in Table 6.

EXAMPLES 19–21

The procedures of Examples 16 to 18, respectively, were repeated with the exception that ammeline was employed in place of the melamine used therein. Table 6 will indicate the results.

TABLE 6

| Examples | Amounts of Gases Generated (mg) |
| --- | --- |
| Example 16 | 0.150 |
| Example 17 | 0.040 |
| Example 18 | 0.017 |
| Example 19 | 0.101 |
| Example 20 | 0.004 |
| Example 21 | 0.017 |
| Comparative Example 14 | 0.806 |
| Comparative Example 15 | 0.018 |
| Comparative Example 16 | 0.033 |

EXAMPLE 22

Two grams of melamine powders were introduced into a 40×50 mm polyethylene bag having a number of small openings and a film thickness of 0.15 mm. One hundred grams of the trichloroisocyanuric acid used in Example 16 were placed in a 150×200 mm high density polyethylene bag having a film thickness of 0.15 mm. The bag containing melamine powders was placed together with the trichlorosiocyanuric acid in the bag and the open end of the bag was then heat sealed. The heat sealed bag was further placed in a 100×150×200 mm craft board paper box having a thickness of 3 mm. The box was then closed and stored in a place where the temperature and the humidity were maintained at 40° C. and a relative humidity of 80 percent for 40 days.

Observations were made with respect to the deterioration of the box, the amounts of gases generated upon decomposition, and the transformation of the solid chlorinating agent. The degree to which the box is deteriorated is determined for the brittleness of the box by operator's finger pressure. The amounts of the gases generated were determined by the measurement of chlorine, nitrogen chloride and chlorine oxide present in the bag by means of a detecting tube. The extent to which the solid chlorinating agent was transformed was determined by calculating the decomposition rate of the effective constituents by a iodometry process. The results will be indicated in Table 7.

COMPARATIVE EXAMPLE 17

The procedure of Example 22 was repeated with the exception that the bag containing melamine powders was not employed. The results will be shown in Table 7.

TABLE 7

| Examples | Deterioration of Box | Amount of Gases Generated | Transformation of Agent |
| --- | --- | --- | --- |
| Example 22 | None Remarkable | 50 p.p.m. | 1.4% |
| Comparative Example 17 | Deterioration Found | 450 p.p.m. | 2.5% |

EXAMPLES 23–25

One hundred parts by weight of high density polyethylene and 20 parts by weight of melamine powders having a thickness of 0.15 mm were mixed in molten state and molded into a sheet which was then shaped into a 150×250 mm bag. One hundred grams each of the solid chlorinating agents as used in Examples 16 to 18, respectively, were separately packed into the bag and the bag was heat sealed. The heat sealed bag was stored for 30 days at 40° C. and a relative humidity of 80 percent.

The bag so stored was measured in the same manner as in Example 22. The results will be indicated in Table 8.

COMPARATIVE EXAMPLES 18–20

The procedures of Examples 23–25, respectively, were repeated with the exception that there was not packed the bag containing melamine powders. The results are shown in Table 8.

TABLE 8

| Examples | Amount of Gases Generated (ppm) | Transformation of Agent (%) |
| --- | --- | --- |
| Example | | |
| 23 | 60 | 1.6 |
| 24 | 15 | 4.6 |
| 25 | 25 | 5.5 |
| Comparative Example | | |
| 18 | 650 | 3.0 |
| 19 | 90 | 7.7 |
| 20 | 80 | 10.4 |

We claim:

1. A method of storing a solid chlorinating agent selected from the group consisting of trichlorinated isocyanuric acid, dichlorinated isocyanuric acid, sodium or potassium dichlorinated isocyanurate, calcium hypochlorite or sodium chlorite in a closed container comprising storing said solid chlorinating agent together with a storage stabilizer selected from the group consisting of trisodium phosphate, ferrous oxide, melamine, ammeline, ammelide and a mixture thereof, said storage stabilizer being brought into contact with the gases from said solid chlorinating agent within the container but not with said solid chlorinating agent itself.

2. The method of claim 1, wherein the storage stabilizer is in a form of granules, powders or tablets.

3. The method of claim 2, wherein the storage stabilizer is employed in an amount of about 0.1 percent to about 10 percent by weight with respect to the solid chlorinating agent.

4. A method of storing a solid chlorinating agent selected from the group consisting of trichlorinated isocyanuric acid, dichlorinated isocyanuric acid, sodium dichlorinated isocyanurate, potassium dichlorinated isocyanurate, calcium hypochlorite, and sodium chlorite in a closed container, comprising storing said solid chlorinating agent in a closed container comprised of a composition consisting essentially of a plastic material and a storage stabilizer selected from the group consisting of trisodium phosphate, calcium oxide, magnesium oxide, ferrous oxide, melamine, ammeline, ammelide, and a mixture thereof.

5. The method of claim 4 wherein the storage stabilizer is employed in an amount of about 0.1% to about 10% by weight with respect to the solid chlorinating agent.

6. An article for storage comprising a solid chlorinating agent selected from the group consisting of trichlorinated isocyanuric acid, dichlorinated isocyanuric acid, sodium dichlorinated isocyanurate, potassium dichlorinated isocyanurate, calcium hypochlorite, and sodium chlorite in a closed container composed of a composition consisting essentially of a plastic material and a storage stabilizer selected from the group consisting of trisodium phosphate, calcium oxide, magnesium oxide, ferrous oxide, melamine, ammeline, ammelide, and a mixture thereof.

7. The article of claim 6 wherein the storage stabilizer is employed in an amount of about 0.1% to about 10% by weight with respect to the solid chlorinating agent.

8. The method of claim 4 or 5, wherein the storage stabilizer is employed as a composition finely dispersed in a plastic material.

9. The method of claim 8, wherein the plastic material is a polymer or copolymer of ethylene, a polymer or copolymer of propylene, a polymer or copolymer of vinyl chloride or a polymer or copolymer of vinylidene chloride or a mixture thereof.

10. The method of claim 9, wherein the amount of the storage stabilizer is from about 10 to 60 percent by weight in the composition.

11. The method of claim 9, wherein the composition is in a form of granules, pellets, filaments, films, sheets, or plates.

12. The method of claim 1, 2 or 3, wherein a package containing the storage stabilizer having an opening small enough to permit the permeation of gases, but disallow the passing through of both of the solid chlorinating agent and the storage stabilizer is placed together with the solid chlorinating agent in a space defined in a closed container.

13. A method of claim 8, where the storage stabilizer as a composition in the form of granule or pellet, filament, film, sheet or plate is placed together with the solid chlorinating agent in a space defined in the closed container.

14. A method of claim 8, wheren the solid chlorinating agent is contained in a container composed of the composition of the storage stabilizer.

15. A method of claim 14, wherein the container containing the solid chlorinating agent is packed in another container.

16. An article for storage comprising a solid chlorinating agent selected from the group consisting of trichlorinated isocyanuric acid, dichlorinated isocyanuric acid, sodium or potassium dichlorinated isocyanurate, calcium hypochlorite or sodium chlorite and a storage stabilizer selected from the group consisting of trisodium phosphate, ferrous oxide, melamine, ammeline, ammelide and a mixture thereof in a closed container, said storage stabilizer being arranged to be into contact with gases from said solid chlorinating agent within the closed container but not in contact with said solid chlorinating agent.

17. The article of claim 8, wherein the storage stabilizer is in a form of granules, powders or tablets.

18. The article of claim 17, wherein the storage stabilizer is employed in an amount of about 0.1 percent to about 10 percent by weight with respect to the solid chlorinating agent.

19. The article of claim 6 or 7, wherein the storage stabilizer is employed as a composition in which the storage stabilizer is finely dispersed in a plastic material.

20. The article of claim 19 wherein the storage stabilizer is in the form of a closed container in which the solid chlorinating agent is stored.

21. The article of claim 17, wherein the storage stabilizer is in a form of a closed container in which the solid chlorinating agent is stored.

22. The article of claim 19, wherein the plastic material is a polymer or copolymer of ethylene, a polymer or copolymer of propylene, a polymer or copolymer of vinyl chloride or a polymer or copolymer of vinylidene chloride or a mixture thereof.

23. The article of claim 19, wherein the amount of the storage stabilizer is from about 10 to 60 percent by weight in the composition.

24. The article of claim 15, wherein the composition is in a form of powders, filaments, films, sheets, or plates.

25. The article of claim 17, wherein the storage stabilizer is contained in a package having an opening small enough to permit the permeation of gases, but disallow the passing through of both of the solid chlorinating agent, said package being placed together with the solid chlorinating agent in a space defined in a closed container.

26. The article of claim 17, where the storage stabilizer as a composition in the form of granules, pellets, filaments, films, sheets or plates is placed together with the solid chlorinating agent in a space defined in the closed container.

27. The article of claim 19, wherein the solid chlorinating agent is contained in a container composed of the composition of the storage stabilizer.

28. The article of claim 27, wherein the container containing the solid chlorinating agent is packed in another container.

* * * * *